(12) United States Patent
Sugata

(10) Patent No.: US 11,051,717 B2
(45) Date of Patent: Jul. 6, 2021

(54) LOAD DETERMINATION METHOD

(71) Applicant: TOYOTA JIDOSHA KABUSHIKI KAISHA, Toyota (JP)

(72) Inventor: Hikaru Sugata, Miyoshi (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 678 days.

(21) Appl. No.: 14/887,835

(22) Filed: Oct. 20, 2015

(65) Prior Publication Data

US 2016/0150999 A1    Jun. 2, 2016

(30) Foreign Application Priority Data

Dec. 1, 2014    (JP) .............................. JP2014-242789

(51) Int. Cl.
| | | |
|---|---|---|
| *A61B 5/103* | (2006.01) | |
| *A61H 3/00* | (2006.01) | |
| *B25J 13/08* | (2006.01) | |
| *B25J 9/00* | (2006.01) | |
| *A61F 2/70* | (2006.01) | |
| *A61F 2/60* | (2006.01) | |
| *A61F 2/76* | (2006.01) | |

(52) U.S. Cl.
CPC .............. *A61B 5/1036* (2013.01); *A61F 2/70* (2013.01); *A61H 3/00* (2013.01); *B25J 9/0006* (2013.01); *B25J 13/085* (2013.01); *A61F 2002/607* (2013.01); *A61F 2002/7635* (2013.01)

(58) Field of Classification Search
None
See application file for complete search history.

(56) References Cited

U.S. PATENT DOCUMENTS

| 6,018,705 | A | | 1/2000 | Gaudet et al. |
| 6,047,201 | A | * | 4/2000 | Jackson, III ......... A61B 5/0002 128/903 |
| 6,052,654 | A | | 4/2000 | Gaudet et al. |
| 6,176,840 | B1 | * | 1/2001 | Nishimura ......... A61H 23/0245 601/2 |
| 2003/0073886 | A1 | * | 4/2003 | Yanagidaira ............. A61B 5/18 600/300 |

(Continued)

FOREIGN PATENT DOCUMENTS

| JP | 2009-160392 A | 7/2009 |
| JP | 2012-235929 A | 12/2012 |

(Continued)

*Primary Examiner* — Matthew Kremer
(74) *Attorney, Agent, or Firm* — Oliff PLC

(57) ABSTRACT

A load determination method determines, based on a load acting on a leg part of a user that is detected, whether the leg part is in a loaded state, which is a ground-contact state, or an unloaded state, which is an idling leg state, in which the load determination method determines that the leg part is in the loaded state instead of determining that the leg part is in the unloaded state even when the load acting on the leg part of the user that is detected becomes smaller than a threshold at which it is determined that the state of the leg part has been switched from the loaded state to the unloaded state within a predetermined period after it is determined that the state of the leg part has been switched from the unloaded state to the loaded state.

12 Claims, 11 Drawing Sheets

(56) References Cited

U.S. PATENT DOCUMENTS

| | | | |
|---|---|---|---|
| 2005/0077856 A1* | 4/2005 | Takenaka | B25J 19/0091 318/568.12 |
| 2005/0283257 A1* | 12/2005 | Bisbee, III | A61F 2/70 623/24 |
| 2008/0139968 A1* | 6/2008 | Endo | A61B 5/04888 600/595 |
| 2008/0275349 A1* | 11/2008 | Halperin | A61B 5/0205 600/484 |
| 2010/0010381 A1* | 1/2010 | Skelton | A61B 5/1116 600/587 |
| 2010/0114330 A1* | 5/2010 | Shishido | A61H 3/008 623/27 |
| 2010/0271051 A1 | 10/2010 | Sankai et al. | |
| 2012/0016276 A1* | 1/2012 | Doi | A61H 1/024 601/34 |
| 2013/0060349 A1* | 3/2013 | Thorsteinsson | A61F 5/0102 623/55 |

FOREIGN PATENT DOCUMENTS

| | | |
|---|---|---|
| JP | 2013-072729 A | 4/2013 |
| JP | 2014-068868 A | 4/2014 |
| JP | 2014-184047 A | 10/2014 |
| JP | 2014-184086 A | 10/2014 |
| WO | 2009/084387 A1 | 7/2009 |

* cited by examiner

RELATED ART

LOAD DETERMINATION METHOD

INCORPORATION BY REFERENCE

This application is based upon and claims the benefit of priority from Japanese patent application No. 2014-242789, filed on Dec. 1, 2014, the disclosure of which is incorporated herein in its entirety by reference.

BACKGROUND OF THE INVENTION

1. Field of the Invention

The present invention relates to a load determination method, and more specifically, to a load determination method to determine whether a leg part is in a loaded state, which is a ground-contact state, or is in an unloaded state, which is an idling leg state based on a load acting on the leg part of the user.

2. Description of Related Art

A load determination method is employed, for example, in a wearable robot that assists the gait of a user, and in order to provide this assist, the load determination method determines whether the leg part is in a loaded state, which is a ground-contact state, or in an unloaded state, which is an idling leg state.

As shown in FIG. 10, a typical load determination method determines whether a previous determination result is the loaded state (S101). When it is determined that the previous determination result is the loaded state (YES in S101), it is determined whether the load acting on the leg part (e.g., sole) of the user is smaller than a threshold at which it is determined that the state of the leg part has been switched from the loaded state to the unloaded state (unload determination threshold) (S102). When the load acting on the leg part of the user is smaller than the unload determination threshold (YES in S102), it is determined that the leg part is in the unloaded state (S103). On the other hand, when the load acting on the leg part of the user is equal to or larger than the unload determination threshold (NO in S102), it is determined that the loaded state is being kept (S104).

When the previous determination result is the unloaded state (NO in S101), it is determined whether the load acting on the leg part of the user is larger than the threshold at which it is determined that the state of the leg part has been switched from the unloaded state to the loaded state (load determination threshold) (S105). When the load acting on the leg part of the user is larger than the load determination threshold (YES in S105), it is determined that the leg part is in the loaded state (S104). On the other hand, when the load acting on the leg part of the user is equal to or smaller than the load determination threshold (NO in S105), it is determined that the unloaded state is being kept (S103).

Japanese Unexamined Patent Application Publication No. 2014-184086 discloses a walking assist device that determines an assist force applied to right and left knee joints based on the load acting on the right and left soles of the user.

According to the typical load determination method, when the detection accuracy of the load acting on the leg part of the user decreases according to the way the user puts the heel thereof on the ground during a walk and the load that is detected becomes smaller than the unload determination threshold even for a moment as shown in FIG. 11, the loaded state is erroneously determined to be the unloaded state.

SUMMARY OF THE INVENTION

The present invention has been made in order to solve the above problem and aims to provide a load determination method capable of suppressing an erroneous determination when it is being determined whether a leg part of a user is in a loaded state or not.

A load determination method according to one embodiment of the present invention determines, based on a load acting on a leg part of a user that is detected, whether the leg part is in a loaded state, which is a ground-contact state, or an unloaded state, which is an idling leg state, in which the load determination method determines that the leg part is in the loaded state instead of determining that the leg part is in the unloaded state even when the load acting on the leg part of the user that is detected becomes smaller than a threshold at which it is determined that the state of the leg part has been switched from the loaded state to the unloaded state within a predetermined period after it is determined that the state of the leg part has been switched from the unloaded state to the loaded state.

In the above load determination method, the load acting on the leg part of the user is preferably detected by a uniaxial load sensor.

As described above, it is possible to provide a load determination method capable of suppressing an erroneous determination when it is being determined whether a leg part of a user is in a loaded state or not.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

Hereinafter, with reference to the accompanying drawings, best modes to achieve the present invention will be described. It should be noted that the present invention is not limited to the following embodiments. Further, for the sake of clarity of the description, the following description and the drawings are simplified as appropriate.

First Embodiment

Figure 1:
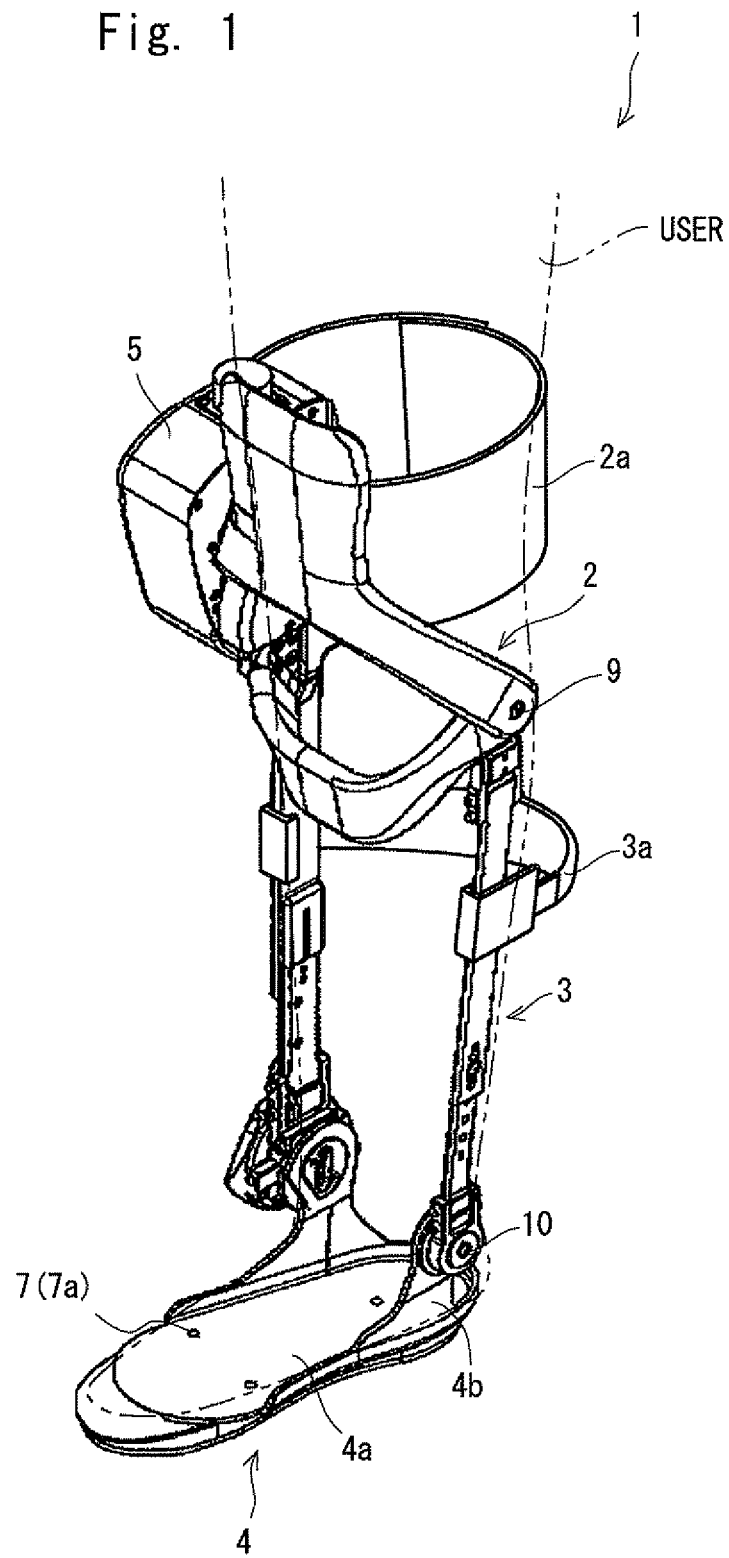
FIG. 1 is a diagram schematically showing a state in which a wearable robot is attached to a knee joint of a user according to a first embodiment.
Figure 2:
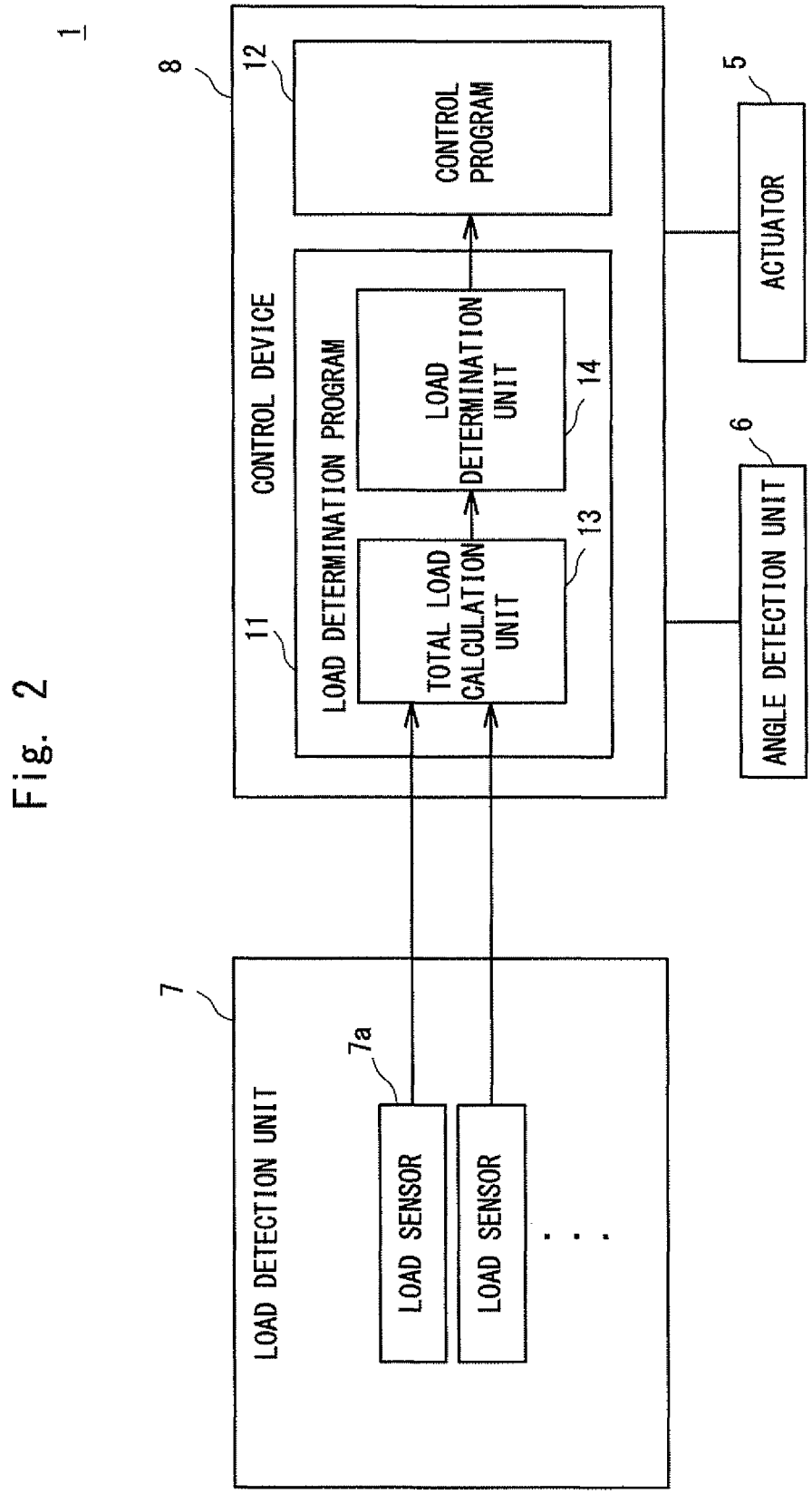
FIG. 2 is a block diagram showing a control system of the wearable robot according to the first embodiment.
Figure 3:
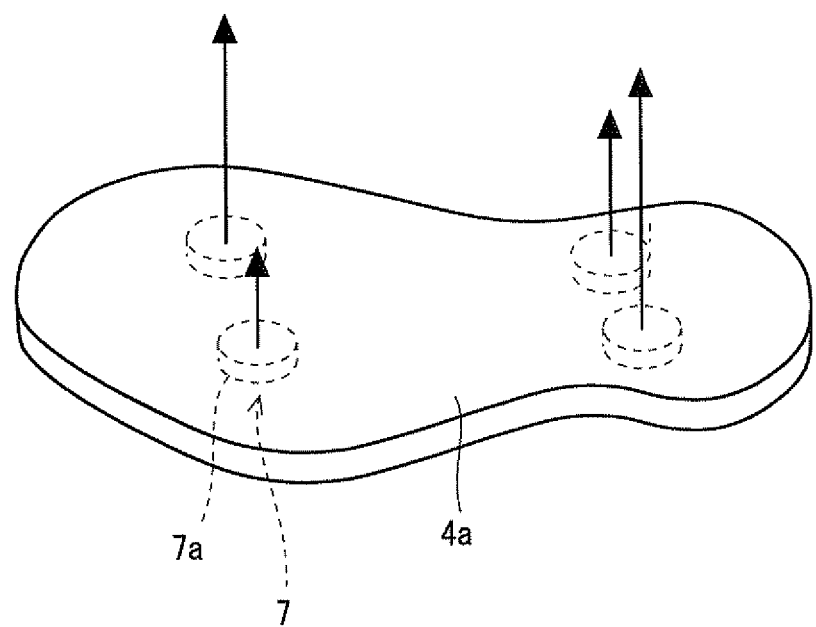
FIG. 3 is a diagram showing an arrangement of load sensors of a load detection unit.

First, the basic structure of a wearable robot in which a load determination method according to this embodiment is executed will be described. FIG. 1 is a diagram schematically showing a state in which a wearable robot is attacked to a knee joint of a user according to this embodiment. FIG. 2 is a block diagram showing a control system of the wearable robot according to this embodiment. FIG. 3 is a diagram showing an arrangement of load sensors of a load detection unit.

As shown in FIGS. 1 and 2, a wearable robot 1 includes a first link 2, a second link 3, a foot part 4, an actuator 5, an angle detection unit 6, a load detection unit 7, and a control device 8. The first link 2 is fixed to the thigh part of the user through a fixing band 2a. The second link 3 is fixed to the shank part of the user through a fixing band 3a. A lower end part of the first link 2 and an upper end part of the second link 3 are coupled to each other through a shaft 9 extending in the horizontal direction of the wearable robot 1 and the first link 2 and the second link 3 can be relatively rotated around the shaft 9.

The foot part 4 includes a sole supporting part 4a on which the sole of the user is placed. A protruding part 4b that protrudes from the sole supporting part 4a and the lower end part of the second link 3 are coupled to each other through the shaft 10 that extends in the horizontal direction of the wearable robot 1 and the foot part 4 and the second link 3 can be rotated around the shaft 10 relative to each other.

The actuator 5 includes, for example, a motor, a reduction gear and the like, and the driving force of the motor is transmitted to the shaft 9 via the reduction gear so that the first link 2 and the third link 3 are rotated relative to each other.

The angle detection unit 6 is provided, for example, in the actuator 5 and detects a rotation angle of the first link 2 with respect to the second link 3 to output a detection signal to the control device 8. A typical angle detection device can be used as the angle detection unit 6. The angle detection unit 6 may be, for example, an encoder.

The load detection unit 7 includes a plurality of load sensors 7a provided on the upper surface of the sole supporting part 4a of the foot part 4. The load detection unit 7 detects the total load acting on the sole of the user and outputs a detection signal to the control device 8. In this embodiment, a uniaxial load sensor is used as the load sensor 7a. As shown in FIG. 3, right and left load sensors 7a are provided spaced apart from each other in each of a region of the sole supporting part 4a which the ball parts of the sole of the user contact and a region of the sole supporting part 4a which the heel part of the sole of the user contacts.

The control device 8 executes a load determination program 11 or a control program 12 and controls the actuator 5 based on the detection signals input from the angle detection unit 6 and the load detection unit 7.

The load determination program 11 includes a total load calculation unit 13 and a load determination unit 14. The total load calculation unit 13 causes the control device 8 to execute processing for calculating the total load acting on the sole of the user based on the detection signal input from the load detection unit 7.

While the details of the operation of the load determination unit 14 will be described later, the load determination unit 14 causes the control device 8 to execute processing for determining whether the leg part of the user is in a loaded state, which is a ground-contact state, or in an unloaded state, which is an idling leg state based on the total load acting on the sole of the user detected by the load detection unit 7. In a predetermined period of time (unload determination cancel time) after it is determined that the state of the leg part has been switched from the unloaded state to the loaded state (that is, the elapsed time after it is determined that the leg part is in the loaded state), even when the total load acting on the sole is smaller than a threshold at which it is determined that the state of the leg part has been switched from the loaded state to the unloaded state (unload determination threshold), the load determination unit 14 causes the control device 8 to carry out processing for determining that the leg part is in the loaded state instead of determining that the leg part is in the unloaded state.

The control program 12 is a program for executing a normal assist operation and causes the control device 8 to execute processing for controlling the actuator 5 so that the rotation angle of the first link 2 with respect to the second link 3 becomes a predetermined angle based on the detection signal input from the angle detection unit 6.

Figure 4:
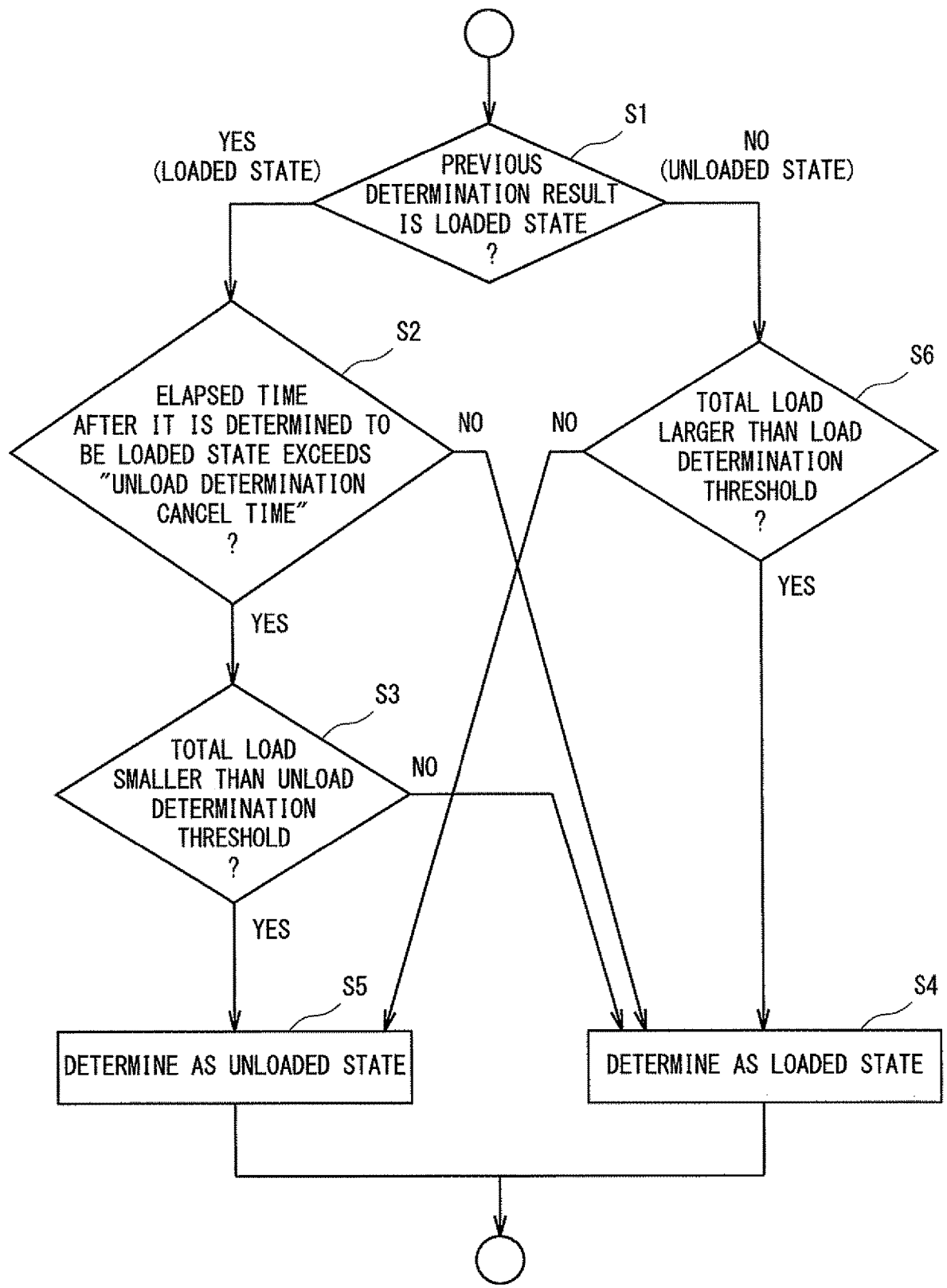
FIG. 4 is a diagram showing a process flow of a load determination program according to the first embodiment.
Figure 5:
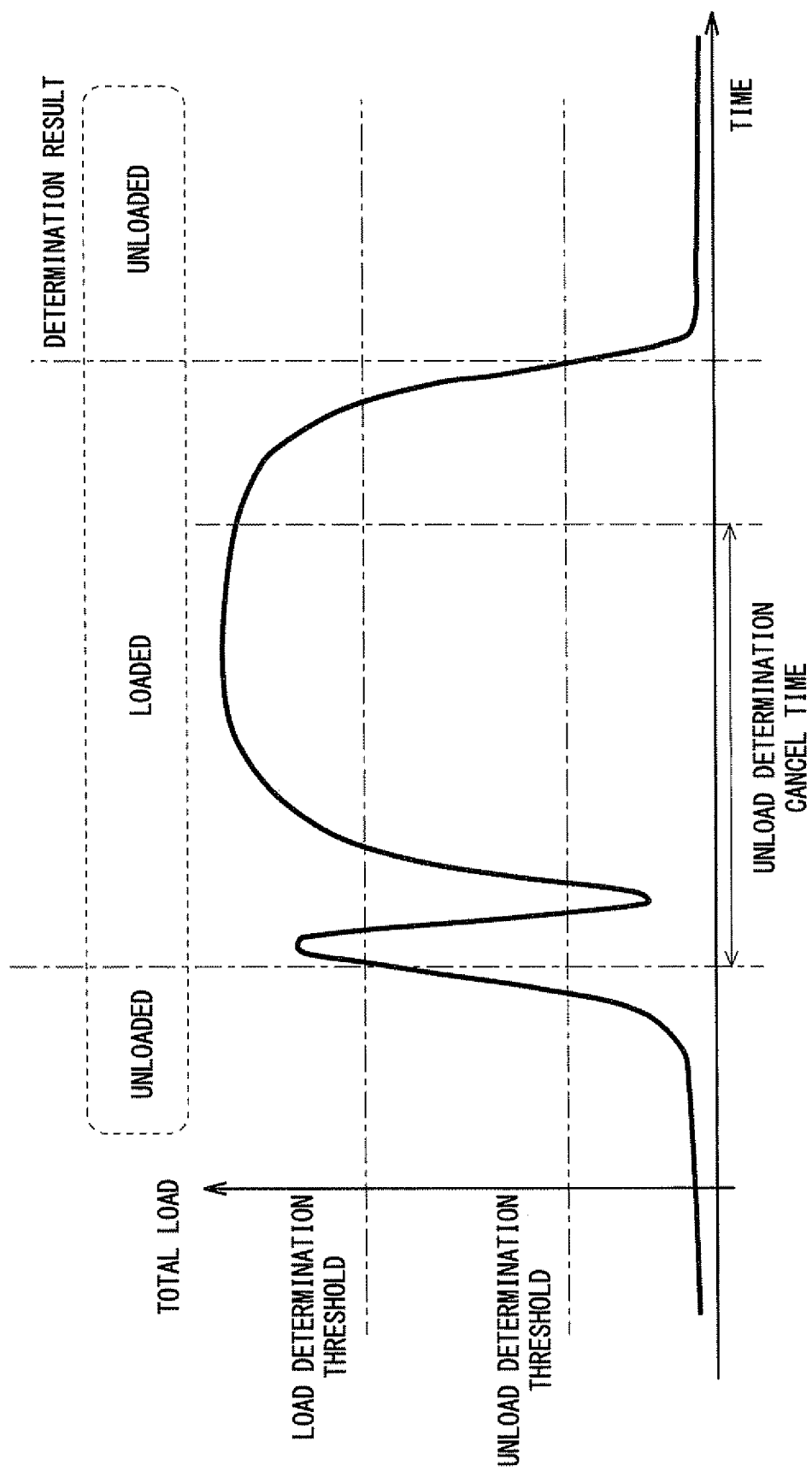
FIG. 5 is a diagram showing a relation between a total load acting on a sole and time and a determination result.

Next, a process flow of the load determination program 11 according to this embodiment will be described. FIG. 4 is a diagram showing a process flow of the load determination program according to this embodiment. FIG. 5 is a diagram showing a relation between the total load acting on the sole and time and a determination result.

First, as shown in FIG. 4, the control device 8 determines whether the previous determination result is the loaded state (S1). When the previous determination result is the loaded state (YES in S1), the control device 8 determines whether the elapsed time after it is determined that the leg part is in the loaded state exceeds the unload determination cancel time (S2). For example, the period from the time at which the user's heel strikes the ground to the time at which the sole completely contacts the ground may be sampled and the unload determination cancel time may be appropriately set based on the result of the sampling. Alternatively, for example, in a normal gait, the period from the time at which the user's heel strikes the ground to the time at which the user's heel leaves the ground may be sampled and the unload determination cancel time may be appropriately set based on the result of the sampling.

When the elapsed time after it is determined that the leg part is in the loaded state exceeds the unload determination cancel time (YES in S2), the control device 8 calculates the total load acting on the sole of the user based on the detection signal from the load detection unit 7 to determine whether the total load that is calculated is smaller than the unload determination threshold (S3).

On the other hand, when the elapsed time after it is determined that the leg part is in the loaded state is equal to or lower than the unload determination cancel time (NO in S2), the control device 8 determines that the leg part is in the loaded state (S4). When it is determined that the leg part is in the loaded state, the control device 8 executes a normal assist control in a state in which the leg part of the user is in the standing leg state.

When the total load that is calculated is smaller than the unload determination threshold (YES in S3), the control device 8 determines that the leg part is in the unloaded state (S5). When it is determined that the leg part is in the unloaded state, the control device 8 executes the normal assist control in a state in which the leg part of the user is in the idling leg state.

On the other hand, when the total load that is calculated is equal to or larger than the unload determination threshold (NO in S3), the control device 8 determines that the leg part is in the loaded state (S4). When it is determined that the leg part is in the loaded state, the control device 8 executes the normal assist control in a state in which the leg part of the user is in the standing leg state.

When the previous determination result is the unloaded state (NO in S1), the control device 8 calculates the total load acting on the sole of the user based on the detection signal from the load detection unit 7 to determine whether the total load that is calculated is larger than a threshold at which it is determined that the state of the leg part has been switched from the unloaded state to the loaded state (load determination threshold) (S6).

When the total load that is calculated is larger than the load determination threshold (YES in S6), the control device 8 determines that the leg part is in the loaded state (S4). When it is determined that the leg part is in the loaded state, the control device 8 executes the normal assist control in a state in which the leg part of the user is in the standing leg state.

On the other hand, when the total load that is calculated is equal to or smaller than the load determination threshold (NO in S6), the control device 8 determines that the leg part is in the unloaded state (S5). When it is determined that the leg part is in the unloaded state, the control device 8 executes the normal assist control in a state in which the leg part of the user is in the idling leg state.

As described above, and as shown in FIG. 5, until the elapsed time after it is determined that the leg part is in the loaded state exceeds the unload determination cancel time, the state of the leg part is determined to be the loaded state even when the total load acting on the sole of the user detected by the load detection unit 7 becomes smaller than the unload determination threshold for a moment. Accordingly, even when the detection accuracy of the load detection unit 7 decreases, for example, due to a gait of the user for a moment and the total load that has been detected is smaller than the unload determination threshold, it is possible to suppress an erroneous determination that the state of the leg part has been switched to the unloaded state.

As described above, when the uniaxial load sensor is used as the load sensor, the detection accuracy of the load detection unit 7 may decrease, for example, due to a gait of the user. When a multiple-axis load sensor is used as the load sensor, it is possible to suppress the decrease in the detection accuracy of the load detection unit 7. However, the multiple-axis load sensor is more expensive and larger in size than the uniaxial load sensor. According to the load determination method according to this embodiment, it is possible to prevent the erroneous determination that the state of the leg part has been switched to the unloaded state even when the uniaxial load sensor is used as the load sensor, whereby it is possible to manufacture the wearable robot 1 inexpensively and to reduce the size of the wearable robot 1.

Second Embodiment

Figure 6:
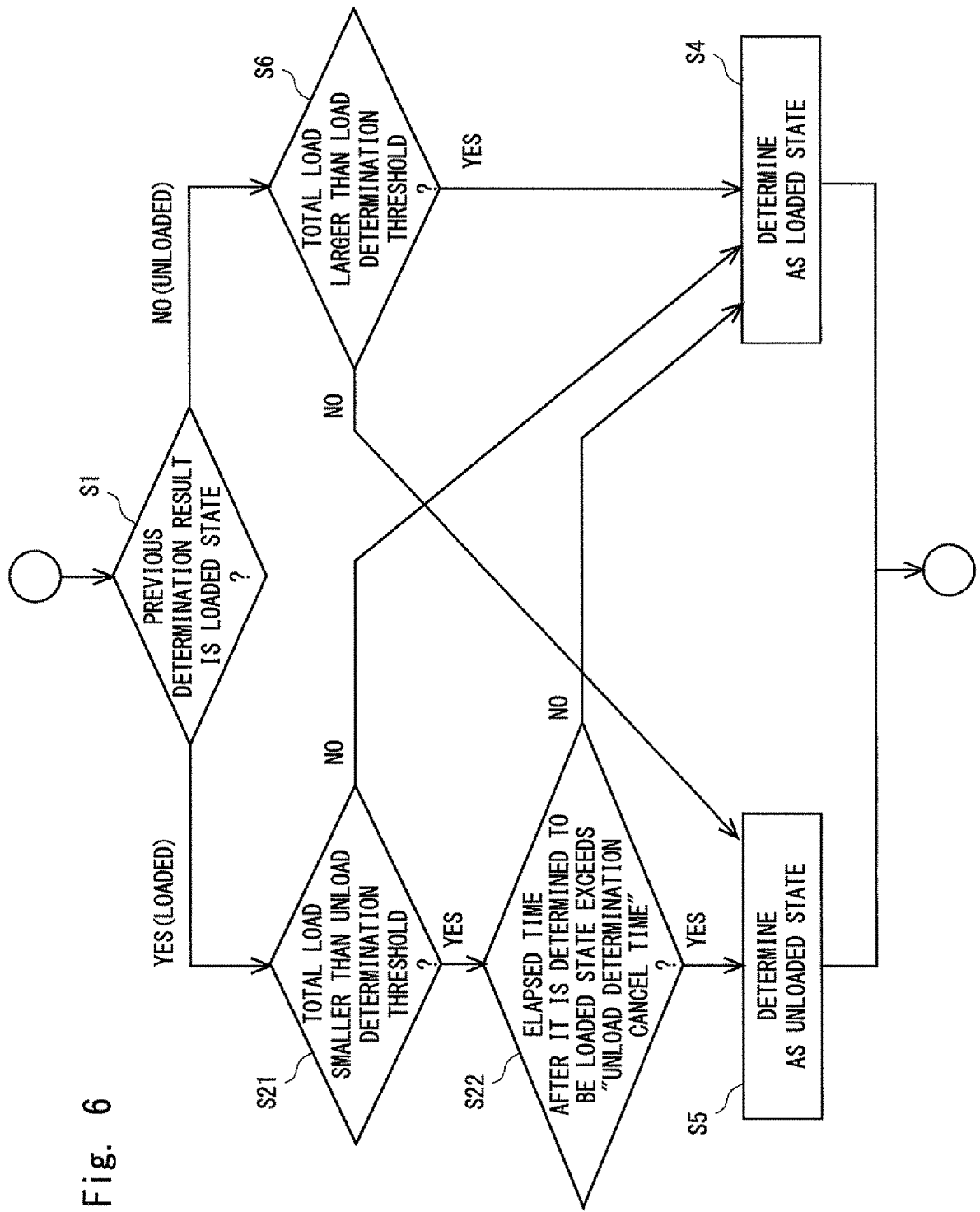
FIG. 6 is a diagram showing a process flow of a load determination program according to a second embodiment.

FIG. 6 is a diagram showing a process flow of a load determination program according to this embodiment. As shown in FIG. 6, compared to the process flow of the load determination program according to the first embodiment, in the process flow of the load determination program according to the second embodiment, the process to determine whether the elapsed time after it is determined that the leg part is in the loaded state exceeds the unload determination cancel time and the process to determine whether the total load that is calculated is smaller than the unload determination threshold may mutually replace each other.

That is, in this embodiment, after the process to determine whether the total load that is calculated is smaller than the unload determination threshold is carried out (S21), the process to determine whether the elapsed time after it is determined that the leg part is in the loaded state exceeds the unload determination cancel time is carried out (S22).

Third Embodiment

Figure 7:
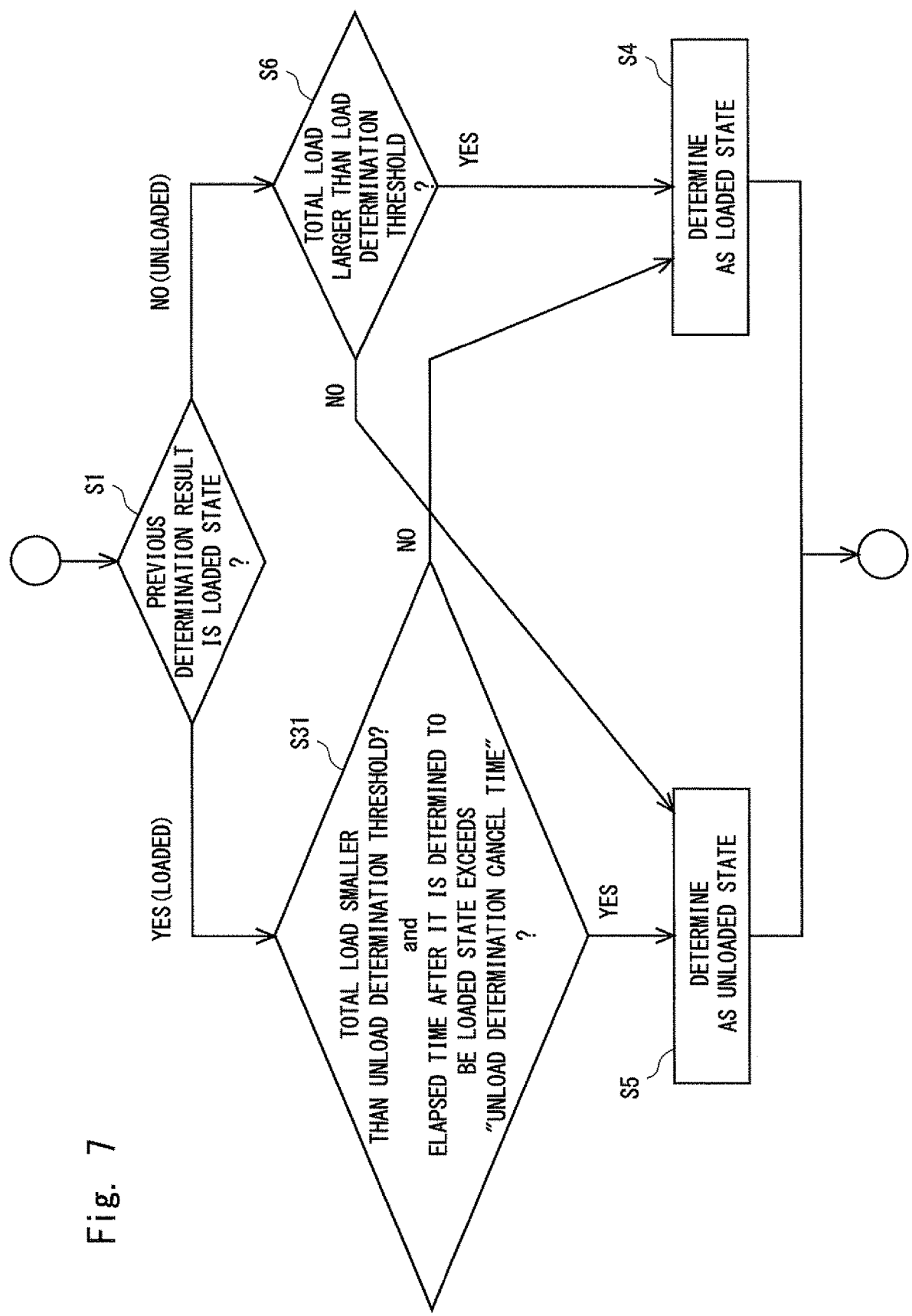
FIG. 7 is a diagram showing a process flow of a load determination program according to a third embodiment.

FIG. 7 is a diagram showing a process flow of a load determination program according to this embodiment. As shown in FIG. 7, compared to the process flow of the load determination program according to the first embodiment, in the process flow of the load determination program according to the third embodiment, the process to determine whether the elapsed time after it is determined that the leg part is in the loaded state exceeds the unload determination cancel time and the process to determine whether the total load that is calculated is smaller than the unload determination threshold can be executed in one process.

That is, in this embodiment, it is determined whether the total load that is calculated is smaller than the unload determination threshold and the elapsed time after it is determined that the leg part is in the loaded state exceeds the unload determination cancel time (S31). When both of the conditions are satisfied (YES in S31), it is determined that the leg part is in the unloaded state (S5). When at least one of the conditions is not satisfied (NO in S31), it is determined that the leg part is in the loaded state (S4).

Fourth Embodiment

It is determined whether the leg part of the user is in the loaded state or the unloaded state based on the load detected by the load detection unit 7 installed in the wearable robot in the above embodiments. When the user conducts, for example, rehabilitation using a treadmill while wearing the wearable robot, it may be determined whether the leg part of the user is in the loaded state or the unloaded state based on the load detected in the load detection unit mounted on the treadmill.

Figure 8:
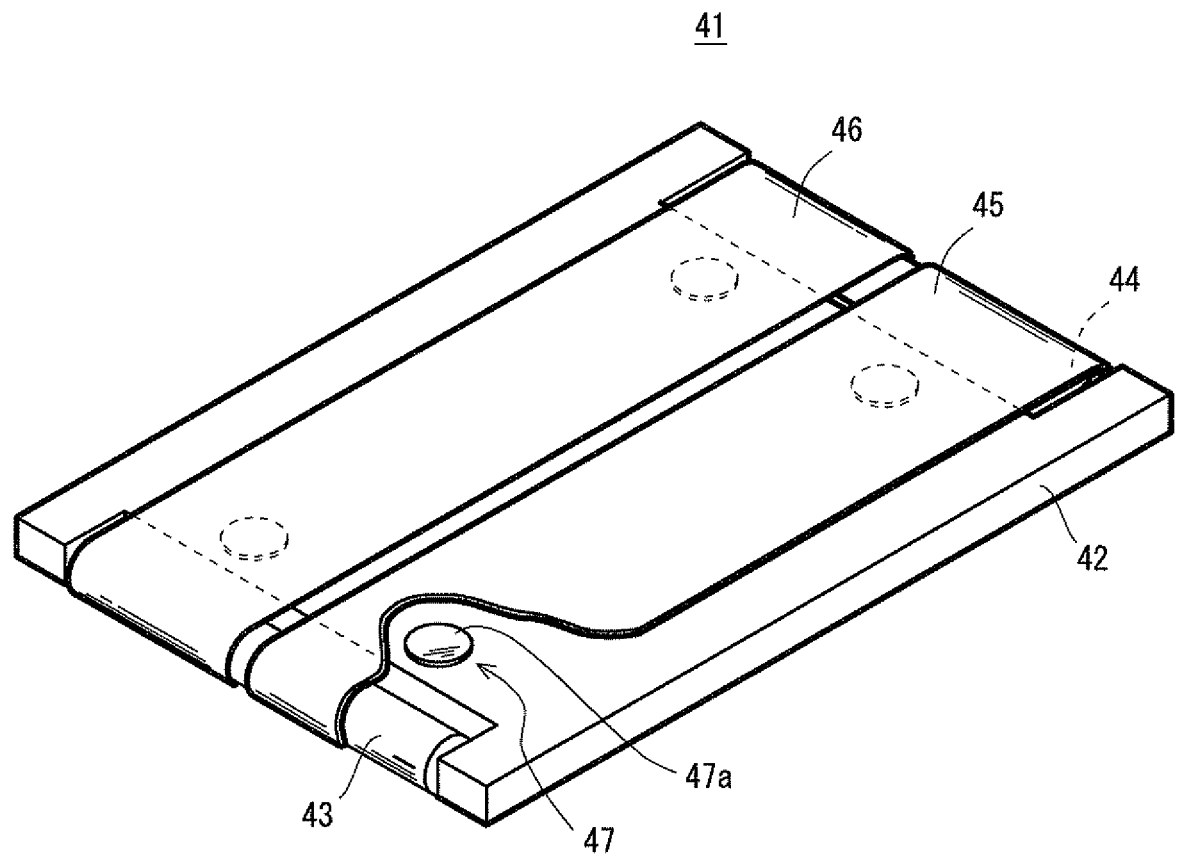
FIG. 8 is a diagram schematically showing a treadmill used in a load determination method according to a fourth embodiment.
Figure 9:
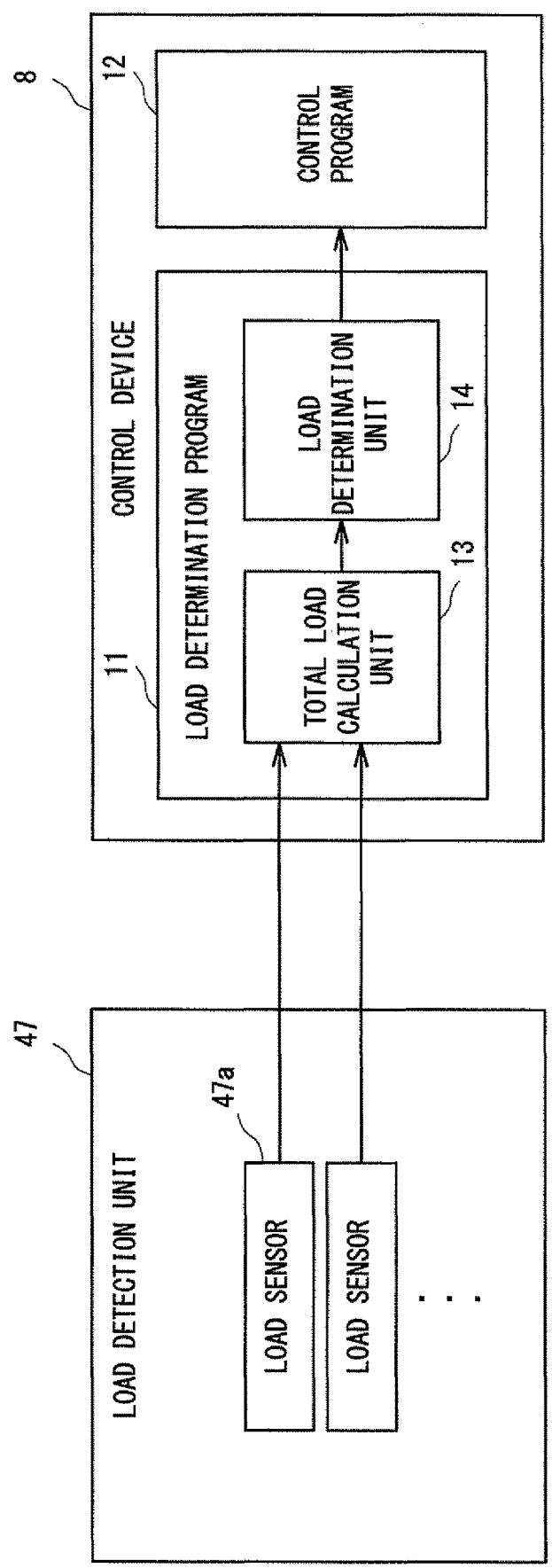
FIG. 9 is a block diagram showing a control system to execute the load determination method according to the fourth embodiment.
Figure 10:
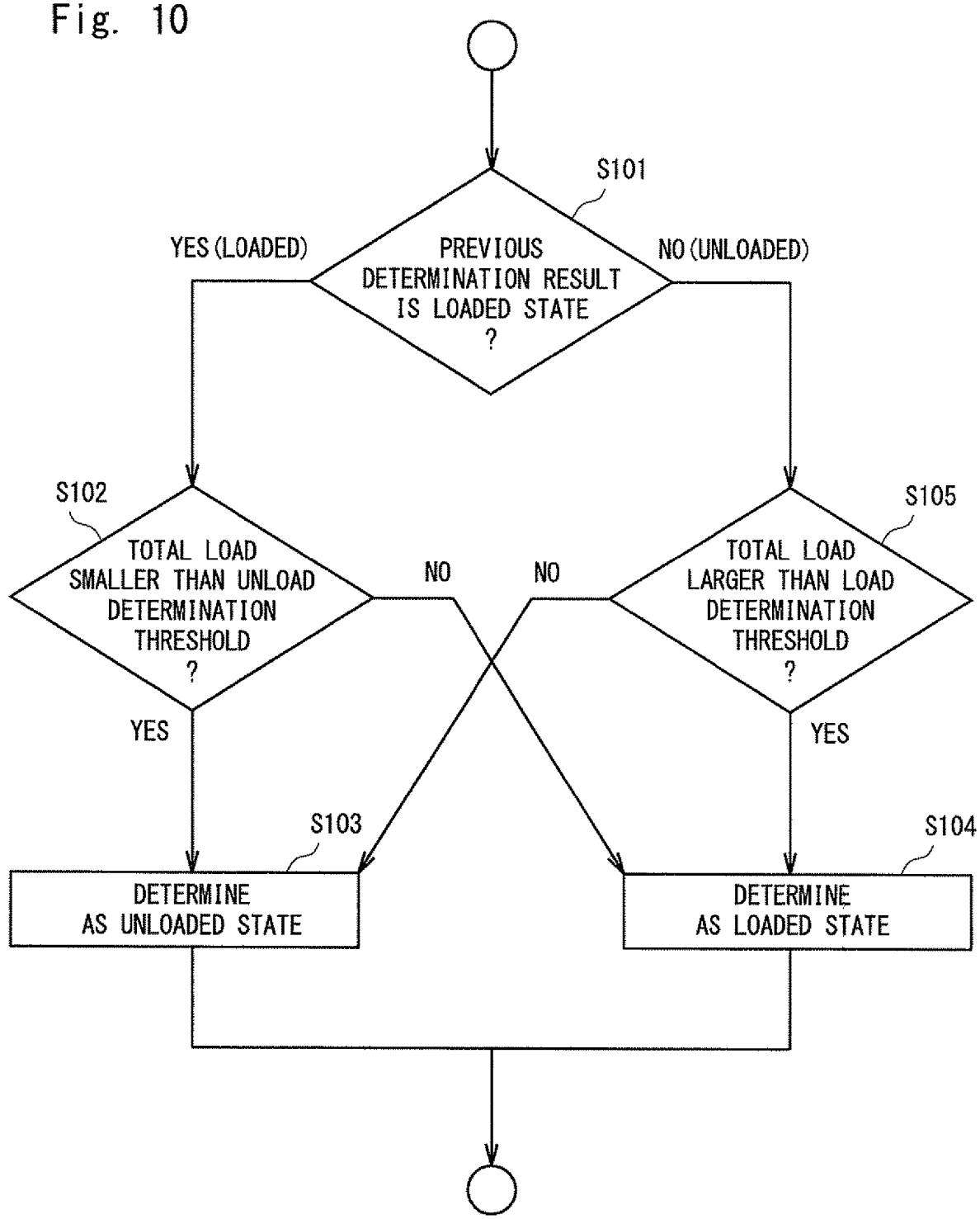
FIG. 10 is a flowchart showing a load determination method according to a related art.
Figure 11:
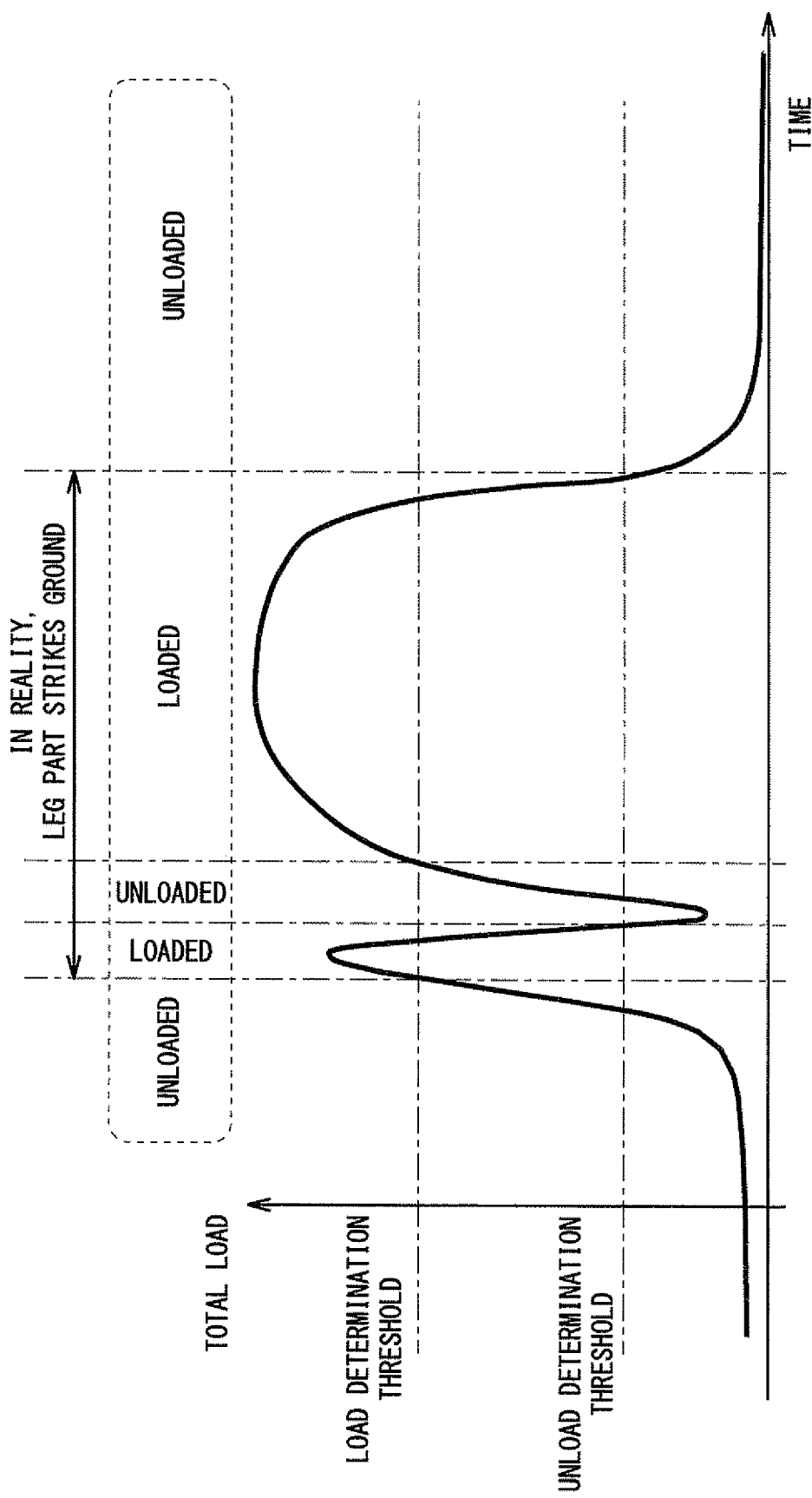
FIG. 11 is a diagram showing a relation between a total load acting on a sole and time and a determination result according to the related art.

FIG. 8 is a diagram schematically showing the treadmill used in the load determination method according to this embodiment. FIG. 9 is a block diagram showing a control system to execute the load determination method according to this embodiment. Since the load determination method according to this embodiment is similar to that in the first embodiment, the detailed descriptions will be omitted.

As shown in FIG. 8, a treadmill 41 according to this embodiment includes rollers 43 and 44 arranged in respective cut-out parts formed in the front and back parts of a frame 42 and endless belts 45 and 46 arranged in the right and left parts of the treadmill 41 in parallel are passed to the rollers 43 and 44 in such a way that the frame 42 is contained inside the endless belts 45 and 46. The rotational driving force is transmitted from a drive apparatus (not shown) to at least one of the rollers 43 and 44, which turns the endless belts 45 and 46.

A plurality of load sensors 47a are provided on the upper surface of the frame 42 of the treadmill 41 as the load detection unit 47 so that the plurality of load sensors 47a are opposed to the inner peripheral surfaces of the endless belts 45 and 46. As shown in FIG. 9, detection signals from the respective load sensors 47*a* are output to the control device 8 of the wearable robot by a wire or wirelessly.

Accordingly, when the user puts the left leg thereof on the endless belt 45 and the right leg thereof on the endless belt 46, the load acting on each of the endless belts 45 and 46 may be detected by the load sensors 47*a*. The control device 8 calculates, based on the detection signals input from the load sensors 47*a*, the total load acting on the left sole of the user and the total load acting on the right sole of the user. The control device 8 then determines, based on the total load acting on the left sole of the user that is calculated or the total load acting on the right sole of the user that is calculated, whether at least the leg part of the user on the side on which the wearable robot is attached is in the loaded state or the unloaded state.

While it is determined whether the leg part of the user is in the loaded state or the unloaded state based on whether the elapsed time after it is determined that the leg part is in the loaded state exceeds the unload determination cancel time in the above embodiments, the present invention is not limited to this case. For example, it may be determined whether the leg part of the user is in the loaded state or the unloaded state based on whether the integral value of the load in the elapsed time after it is determined that the leg part is in the loaded state exceeds the threshold at which it is determined that the state of the leg part has been switched from the loaded state to the unloaded state.

While the determination of the load in the leg part is performed using the plurality of load sensors in the above embodiments, the determination of the load in the leg part may be performed using one load sensor.

While the control method is achieved using software resources in the above embodiments, it may be achieved using hardware resources.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims

What is claimed is:

1. A load determination method for determining whether a wearable leg part attached to a user is in: (i) a loaded state that is a ground-contact state based on whether a weight applied to the wearable leg part is larger than a load determination threshold, or (ii) an unloaded state that is an idling leg state based on whether the weight is smaller than an unload determination threshold, the load determination method comprising:
   measuring, by a sensor connected to the wearable leg part, a total load acting on the wearable leg part over an elapsed period of time;
   in response to a previous determination result indicating that the wearable leg part is in the loaded state, determining whether the elapsed period of time in which the measured total load acts on the wearable leg part exceeds a predetermined unload determination cancel period that prevents an erroneous determination that a state of the wearable leg part has switched to the unloaded state;
   in response to the elapsed period of time being determined as being less than the predetermined unload determination cancel period, determining that the wearable leg part is in the loaded state thereby preventing the erroneous determination that the wearable leg part is in the unloaded state; and
   in response to the elapsed period of time being determined to exceed the predetermined unload determination cancel period and the measured total load being less than the unload determination threshold, determining that the wearable leg part is in the unloaded state.

2. The load determination method according to claim 1, wherein the sensor is a uniaxial load sensor.

3. The load determination method according to claim 1, further comprising:
   determining that the wearable leg part is in the loaded state based on an amount of the measured total load being larger than the load determination threshold and the elapsed period of time being less than the predetermined unload determination cancel period.

4. The load determination method according to claim 1, further comprising:
   determining that the wearable leg part is in the unloaded state based on an amount of the measured total load being less than the unload determination threshold and the elapsed period of time being equal or greater than the predetermined unload determination cancel period.

5. The load determination method according to claim 1, further comprising:
   in response to a previous determination result indicating that the wearable leg part is in the unloaded state and the measured total load being larger than the load determination threshold, determining that the wearable leg part is in the loaded state.

6. The load determination method according to claim 1, further comprising:
   in response to the elapsed period of time exceeding the predetermined unload determination cancel period and the measured total load being larger than the unload determination threshold, determining that the wearable leg part is in the loaded state.

7. A wearable leg part configured to be attached to a user, the wearable leg part comprising:
   a sensor connected to the wearable leg part, the sensor being configured to measure a total load acting on the wearable leg part over an elapsed period of time; and
   a processor programmed to:
     determine whether the wearable leg part is in: (i) a loaded state that is a ground-contact state based on whether a weight applied to the wearable leg part is larger than a load determination threshold, or (ii) an unloaded state that is an idling leg state based on whether the weight is smaller than an unload determination threshold,
     in response to a previous determination result indicating that the wearable leg part is in the loaded state, determining whether the elapsed period of time in which the measured total load acts on the wearable leg part exceeds a predetermined unload determination cancel period that prevents an erroneous determination that a state of the wearable leg part has switched to the unloaded state,
     in response to the elapsed period of time being determined as being less than the predetermined unload determination cancel period, determining that the wearable leg part is in the loaded state thereby preventing the erroneous determination that the wearable leg part is in the unloaded state; and
     in response to the elapsed period of time being determined to exceed the predetermined unload determination cancel period and the measured total load being less than the unload determination threshold, determining that the wearable leg part is in the unloaded state.

8. The wearable leg part according to claim 7, wherein the sensor is a uniaxial load sensor.

9. The wearable leg part according to claim 7, wherein the processor is further programmed to:
   determine that the wearable leg part is in the loaded state based on an amount of the measured total load being larger than the load determination threshold and the elapsed period of time being less than the predetermined unload determination cancel period.

10. The wearable leg part according to claim 7, wherein the processor is further programmed to:
    determine that the wearable leg part is in the unloaded state based on an amount of the measured total load being less than the unload determination threshold and the elapsed period of time being equal or greater than the predetermined unload determination cancel period.

11. The wearable leg part according to claim 7, wherein the processor is further programmed to:
    in response to a previous determination result indicating that the wearable leg part is in the unloaded state and the measured total load being larger than the load determination threshold, determine that the wearable leg part is in the loaded state.

12. The wearable leg part according to claim 7, wherein the processor is further programmed to:
    in response to the elapsed period of time exceeding the predetermined unload determination cancel period and the measured total load being larger than the unload determination threshold, determine that the wearable leg part is in the loaded state.

\* \* \* \* \*